United States Patent
Puntambekar

(10) Patent No.: US 6,800,124 B2
(45) Date of Patent: Oct. 5, 2004

(54) ETHYLENE OXIDE STERILIZATION PROCESS INDICATOR INKS

(75) Inventor: Shobha Shakher Puntambekar, Morganville, NJ (US)

(73) Assignee: Illinois Tool Works Inc., Glenview, IL (US)

( * ) Notice: Subject to any disclaimer, the term of this patent is extended or adjusted under 35 U.S.C. 154(b) by 22 days.

(21) Appl. No.: 10/178,192

(22) Filed: Jun. 24, 2002

(65) Prior Publication Data

US 2003/0235654 A1 Dec. 25, 2003

(51) Int. Cl.$^7$ .............................. C09D 11/00
(52) U.S. Cl. .............. 106/31.32; 106/31.64; 106/31.28
(58) Field of Search ............ 106/31.32, 31.64, 106/31.28; 436/1, 36, 38

(56) References Cited

U.S. PATENT DOCUMENTS

| | | | |
|---|---|---|---|
| 2,998,306 A | | 8/1961 | Huyck et al. |
| 3,098,751 A | | 7/1963 | Huyck et al. |
| 4,145,186 A | | 3/1979 | Andersen |
| 4,166,044 A | * | 8/1979 | Germonprez et al. .... 252/408.1 |
| 4,168,779 A | * | 9/1979 | Yokokoji et al. ........... 206/439 |
| 4,206,844 A | | 6/1980 | Thukamoto et al. |
| 4,362,645 A | * | 12/1982 | Hof et al. ................ 252/408.1 |
| 5,183,742 A | * | 2/1993 | Omoto et al. .................. 435/14 |
| 5,254,473 A | * | 10/1993 | Patel .............................. 436/1 |
| 5,591,400 A | * | 1/1997 | Dektar et al. ................. 422/57 |
| 5,814,327 A | * | 9/1998 | Ito et al. ...................... 424/414 |
| 5,990,199 A | * | 11/1999 | Bealing et al. ............. 523/161 |
| 6,208,880 B1 | * | 3/2001 | Bentsen et al. ............. 600/322 |
| 2003/0199095 A1 | * | 10/2003 | Yuyama et al. ................ 436/1 |
| 2003/0211618 A1 | * | 11/2003 | Patel ........................... 436/38 |

FOREIGN PATENT DOCUMENTS

| | | |
|---|---|---|
| GB | 854 142 A | 11/1960 |
| JP | 57 010902 B | 3/1982 |
| WO | WO 01/10471 A | 2/2001 |

* cited by examiner

Primary Examiner—Mark L. Bell
Assistant Examiner—Veronica F. Faison
(74) Attorney, Agent, or Firm—Dinsmore & Shohl LLP

(57) ABSTRACT

Water-based chemical indicator inks for ethylene oxide sterilization processes and methods for its use. The chemical indicator ink contains at least one pH indicator dye selected from the group consisting of Bromocresol green, Bromophenol blue, Methyl red, Ethyl orange, and combinations thereof. The pH indicator dye undergoes an irreversible color change when exposed to ethylene oxide vapor in the presence of low-temperature steam, but when exposed to other sterilization processes either does not undergo a color change or undergoes a color change that is different than is obtained when exposed to ethylene oxide.

18 Claims, No Drawings

ETHYLENE OXIDE STERILIZATION PROCESS INDICATOR INKS

BACKGROUND OF THE INVENTION

The present invention relates to ethylene oxide sterilization process indicators and, more particularly, to chemical indicator inks that are designed to undergo an irreversible color change when exposed to ethylene oxide vapor in the presence of low-temperature steam, and to methods for indicating that an article has undergone ethylene oxide sterilization processing.

Biological and medical operations such as hospitals, medical laboratories and other allied health facilities, which often come in contact with microorganisms and other microbiological agents, employ a variety of technology to control both infection and contamination. While compositions such as germicides, antiseptics and bacteriostats are effective in controlling widespread growth of biological contaminants, they do not go as far as to completely eliminate these agents.

Since many of the materials and instruments that are used in modern hospitals must be kept sterile, but cannot withstand the heat and/or moisture encountered in a conventional steam sterilization process, there is a growing trend towards the use of an alkylating agent as the sterilization agent. The most popular sterilization alkylating agent presently employed is ethylene oxide gas, generally in an admixture with an inert gaseous diluant such as carbon dioxide, nitrogen, tricloromonofluoromethane, dichlorodifluoromethane, and the like. Ethylene oxide gas can be used as a sporicidal and virucidal agent. Consequently, ethylene oxide sterilization processes are often employed to ensure total eradication of microorganisms.

Since ethylene oxide gas readily diffuses through all of the commonly employed packaging materials and is highly effective in killing microorganisms at temperatures well below those required for heat sterilization techniques, it enables efficient sterilization of many items, particularly those made of thermoplastic materials, which cannot withstand heat sterilization. The process generally involves placing an item in a chamber and subjecting it to ethylene oxide vapor. When used properly, ethylene oxide is not only lethal to all known microorganisms at ordinary temperature, but it is also non-corrosive, readily removed by aeration, easily handled and stored, and has a low toxicity to humans.

Known in the art are methods for indicating that an article has undergone ethylene oxide sterilization. For example, U.S. Pat. Nos. 2,998,306 and 3,098,751 teach methods employing water-based and solvent-based chemical indicators, respectively, which undergo an irreversible color change when placed in an ethylene oxide environment. However, the number of color changes available from these indicators is limited. Moreover, the organic solvents employed in some of these chemical indicators present an environmental hazard. Thus, there is a need for chemical indicator inks that exhibit additional color changes upon exposure to ethylene oxide vapor in the presence of low-temperature steam and do not contain high concentrations of volatile organic compounds.

SUMMARY OF THE INVENTION

The present invention meets this need by providing water-based chemical indicator inks that contain at least one pH indicator dye. The inks are effective in showing whether or not treated materials have been subjected to sterilizing conditions using ethylene oxide as the sterilization medium.

In accordance with one aspect of the present invention, a water-based chemical indicator ink for ethylene oxide sterilization processes is provided containing at least one pH indicator dye selected from the group consisting of Bromocresol green, Bromophenol blue, Methyl red, Ethyl orange, and combinations thereof. The pH indicator dye undergoes an irreversible color change when exposed to ethylene oxide vapor in the presence of low-temperature steam. The low-temperature steam has a temperature of less than about 145° F. Moreover, the pH indicator dye when exposed to other sterilization processes such as formaldehyde gas, high-temperature steam, dry heat, or combinations thereof, either does not undergo a color change or undergoes a color change that is different than is obtained when exposed to ethylene oxide vapor.

The water-based chemical indicator ink can comprise a solution including the pH indicator dye dissolved in water. The water-based chemical indicator ink can further contain a powdered and crystallized hexahydrate metal salt. In addition, the water-based chemical indicator ink can further contain an acidic compound such as citric acid, at least one thickening agent, a white pigment such as titanium dioxide, a binder, and/or a foam suppressor such as an aliphatic polyol blend. The acidic compound retards a color change of the water-based chemical indicator ink. The thickening agent can be selected from the group consisting of hydrous aluminum silicates, hydrous magnesium silicates, and combinations thereof. The binder can be a polymeric material selected from the group consisting of polyvinyl alcohol, methyl cellulose, and combinations thereof.

In accordance with another aspect of the present invention, a method is provided for indicating that an article has undergone ethylene oxide sterilization processing. The method comprises providing a water-based chemical indicator ink containing at least one pH indicator dye selected from the group consisting of Bromocresol green, Bromophenol blue, Methyl red, Ethyl orange, and combinations thereof. The pH indicator dye undergoes an irreversible color change when exposed to ethylene oxide vapor in the presence of low-temperature steam. The method further comprises applying the water-based chemical indicator ink to an article, subjecting the article to a concentration of ethylene oxide vapor in the presence of low-temperature steam, and observing the chemical indicator ink for a color change that is visually indicative of whether the concentration of ethylene oxide vapor has been applied for a time sufficient to sterilize the article.

The method can further comprise measuring the integrated effect of subjecting the article to the concentration of ethylene oxide vapor in the presence of low-temperature steam for the time sufficient to sterilize the article. In addition, the method can comprise applying the water-based chemical indicator ink to a substrate to form an ethylene oxide sterilization process indicator prior to applying the ink to the article. The step of applying the water-based chemical indicator ink to a substrate can be accomplished by printing the ink on the substrate in the shape of squares or insignia to form the indicator. In addition, the indicator can be secured to a package containing the article and subjected to the concentration of ethylene oxide vapor in the presence of low-temperature steam.

Accordingly, it is a feature of the present invention to provide a water-based chemical indicator ink for printing insignia on a substrate that is visually indicative of whether a concentration of ethylene oxide has been applied for a time sufficient to ensure sterilization within a treating chamber or within the contents of a package subjected to ethylene oxide gas treatment therein. It is also a feature of the present invention to provide a printed informative device for ethylene oxide sterilization, which is cost effective, relatively simple to use, resists contaminating the goods being sterilized, and is environmentally friendly. This and other features and advantages of the present invention will become apparent from the following detailed description and the appended claims.

DETAILED DESCRIPTION OF THE INVENTION

The present invention provides water-based chemical indicator inks for ethylene oxide sterilization processes. The water-based chemical indicator ink contains at least one pH indicator dye. The pH indicator dye will undergo a visual, distinct and irreversible color change when exposed to ethylene oxide vapor in the presence of low-temperature steam. Accordingly, the water-based chemical indicator ink composition of the present invention can be applied to a substrate to form an ethylene oxide sterilization process indicator that is effective in signaling whether an article has been subjected to ethylene oxide sterilization processing.

Unlike biological indicators which utilize dried microbes and can be cultured in sterile media following processing to ensure sterilization, the water-based chemical indicator ink of the present invention merely shows that an article has undergone ethylene oxide sterilization processing. It does not indicate whether any microbial contaminants were effectively destroyed. Consequently, it is important for the operator of the ethylene oxide sterilization process to follow correct sterilization protocols.

As discussed in U.S. Pat. No. 3,098,751, the efficacy of sterilization by ethylene oxide depends upon a number of factors, the most important of which are the concentration of the ethylene oxide in the sterilization vessel or chamber, the moisture present, the time of contact with the ethylene oxide, and the temperature of the treatment. Since one of the principal advantages of ethylene oxide sterilization is that it is effective at relatively low temperature, most sterilizers are operated at ambient temperature up to about 145° F. (which falls within the definition of "low-temperature" as used herein). Humidity in the range from 40 to 60% relative humidity (which falls within the definition of "steam" as used herein) has been found to be most effective, and in practice this range can be maintained. The effects of time and concentration are inter-related and generally expressed as the lower the concentration, the longer time of exposure required to effect sterilization.

The telltales of the present invention, as well as the invention described in U.S. Pat. No. 3,098,751, measure the integrated effect of time of exposure, and the concentration of the ethylene oxide, in the presence of water vapor (i.e., "steam"). The telltales depend upon the chemical reaction of ethylene oxide on magnesium chloride, crystallized with water,

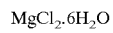

$MgCl_2.6H_2O$ by which magnesium hydroxide and epichlorohydrin are produced.

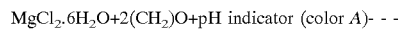

$MgCl_2.6H_2O+2(CH_2)O+pH$ indicator (color A)- - -

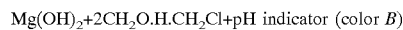

$Mg(OH)_2+2CH_2O.H.CH_2Cl+pH$ indicator (color B)

When a known amount of acid is initially added to the composition, a known minimum amount of ethylene oxide will have been absorbed and reacted with the acid when the mass becomes alkaline, after exposure to moist ethylene oxide. This alkalinity is visually observed when a pH indicator dye in the composition changes from one color when acidic (A) to another color when the composition is alkaline (B).

These reactions can be utilized when the composition is in the form of a dried printing ink, which is applied by the process of printing, particularly by flexographic printing of squares or insignia on a substrate. The freshly applied squares or insignia are allowed to dry, after which the printed indicators are used as telltales to indicate that moist ethylene oxide has been present in sufficient concentration for a long enough time to effectively sterilize the goods or articles contained in the sterilizing vessel or chamber.

The indicator ink consists of a thickened liquid ink base, powdered magnesium chloride with water of crystallization ($MgCl_2.6H_2O$), and a pH indicator dye. However, unlike the flexographic ink of U.S. Pat. No. 3,098,751, the chemical indicator ink of the instant invention, which dries rapidly by evaporation, is water-based. The water-based chemical indicator ink consists generally of:

1) a polymer dissolved in water, 2) a pH indicator dye, 3) a thickener, 4) an acidic compound, and 5) a defoamer.

The present invention provides color changes not contemplated by the prior art. Acidic material used reacts with alkali liberated when ethylene oxide reacts with magnesium chloride. A white pigment is also used with the pH indicator dye to enhance the color change.

In accordance with one embodiment of the present invention, the pH indicator dye can be Bromocresol green (cas. #76-60-8) or 3',3", 5',5"-tetrabromo-m-cresol sulfonephthalein. The chemical structure for this pH indicator dye is:

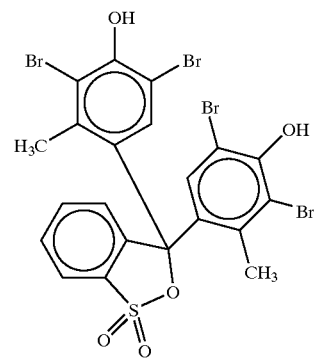

In accordance with another embodiment of the present invention, the pH indicator dye can be Bromophenol blue (cas. #115-39-9) or 3',3", 5',5"-tetrabromophenol-sulfonephthalein. The chemical structure for this pH indicator dye is:

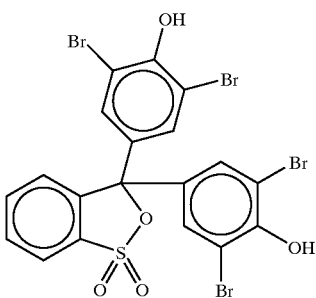

In accordance with another embodiment of the present invention, the pH indicator dye can be Ethyl orange sodium salt (cas. #62758-12-7) or [4-(4-diethylaminophenylazo) benzenesulfonic acid, sodium salt]. The chemical structure for this pH indicator dye is:

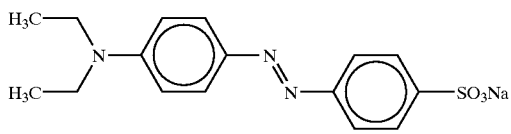

In accordance with another embodiment of the present invention, the pH indicator dye can be Methyl red sodium salt (cas. #845-10-3) or {2-[4-(dimethylamino)phenylazo] benzoic acid}sodium salt. The chemical structure for this pH indicator dye is:

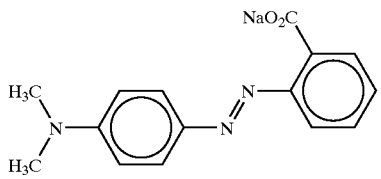

Each of the above-mentioned pH indicator dyes, when subjected to ethylene oxide, exhibit a distinct and irreversible color change. The color changes are visually very marked. Consequently, it is readily apparent when viewing the ethylene oxide sterilization process indicator of the present invention whether the materials associated therewith have been subjected to ethylene oxide sterilization processing. Individual pH indicator dyes, each exhibiting a distinct color change, can be combined to form a single chemical indicator ink that exhibits its own distinct color change. The colors of the individual and combined pH indicator dyes of the present invention both before and after exposure to ethylene oxide (ETO) vapor are set forth in Table 1 below.

TABLE 1

| pH Indicator Dye(s) Before and After Exposure to ETO Vapor | | |
|---|---|---|
| pH Indicator No. Dye(s) | Color Before Exposure to ETO | Color After Exposure to ETO |
| 1 Bromocresol green + Methyl red | Brick red | Blue |
| 2 Bromophenol blue + Ethyl orange | Orange | Blue |
| 3 Ethyl orange | Pink | Orange |
| 4 Bromophenol blue | Yellow | Blue |

TABLE 1-continued

| pH Indicator Dye(s) Before and After Exposure to ETO Vapor | | |
|---|---|---|
| pH Indicator No. Dye(s) | Color Before Exposure to ETO | Color After Exposure to ETO |
| 5 Bromophenol blue + Methyl red | Brick red | Purple |
| 6 Bromocresol green | Orange | Green |

The water-based chemical indicator ink of the present invention can be an aqueous ink solution, wherein the pH indicator dye is dissolved in water. The water-based chemical indicator ink can further include a powdered and crystallized hexahydrate metal salt that provides water so as to facilitate the sterilization reaction, and/or an acidic compound, i.e., citric acid, which acts as a color retarder ingredient. Further, the water-based chemical indicator ink can include a thickening agent such as talc (hydrous silicates of magnesium or aluminum). A white pigment such as titanium dioxide can be added to the water-based chemical indicator ink as a brightener for the pH indicator dye. Polyvinyl alcohol, methyl cellulose, and/or other polymeric materials can also be added to assist in binding and stabilizing the water-based chemical indicator ink until use. Moreover, the water-based chemical indicator ink can further include a foam suppressor such as an aliphatic polyol blend.

In accordance with another aspect of the present invention, a method is provided for indicating that an article has undergone ethylene oxide sterilization processing, which comprises providing a water-based chemical indicator ink as described herein, applying the ink to an article, subjecting the article to a concentration of ethylene oxide vapor in the presence of low-temperature steam, and observing the ink for a color change that is visually indicative of whether the concentration of ethylene oxide vapor has been applied for a time sufficient to sterilize the article. The method can further comprise measuring the integrated effect of subjecting the article to the concentration of ethylene oxide vapor in the presence of low-temperature steam for the time sufficient to sterilize the article. In addition, the method can comprise applying the ink to a substrate to form an ethylene oxide sterilization process indicator prior to applying it to the article, or printing the ink on the substrate in the shape of squares or insignia. Moreover, the method can comprise securing the ethylene oxide sterilization process indicator to a package containing an article and subjecting the package to ethylene oxide sterilization.

In order that the invention may be more readily understood, reference is made to the following example, which is intended to illustrate the invention, but not limit the scope thereof.

The chemical indicator inks used in the example that follows were prepared with the ingredients listed in Table 2 below.

TABLE 2

| Ingredients for Chemical Indicator Inks | |
|---|---|
| Ingredient | Amount (g) |
| Water | 39.02 |
| 15% Polyvinyl alcohol | 39.02 |
| Thickeners | 7.57 |
| Hexahydrate metal salt | 7.28 |
| Citric acid | 3.989 |

TABLE 2-continued

Ingredients for Chemical Indicator Inks

| Ingredient | Amount (g) |
|---|---|
| pH indicators | 1.04 |
| Methyl cellulose | 1.03 |
| Foam suppressor | 0.033 |

Portions of the resulting chemical indicator inks were tested by exposure to ethylene oxide vapor in the presence of low-temperature steam for 4 hours at 125° F. (see Table 1 above). The gas concentration was 600 mg/l of ethylene oxide and nitrogen. Further portions of the chemical indicator inks were subjected to: 1) steam autoclave sterilization in the absence of ethylene oxide for 20 minutes at 250° F.; 2) dry heat for 30 minutes at 284° F.; and 3) steam formaldehyde sterilization. These different sterilization processes resulted in either no color change or a different color change than was obtained from exposure to ethylene oxide. The results of these different sterilization methods are shown in Table 3 below.

TABLE 3 pH Indicator Dye(s) Before and After Exposure to Different Sterilization Methods

| No. | pH Indicator Dye(s) | Original Color | Dry Heat Sterilization | Steam Sterilization | Formaldehyde Sterilization |
|---|---|---|---|---|---|
| 1 | Bromocresol green + Methyl red | Brick red | No color change | No color change | No color change |
| 2 | Bromophenol orange + Ethyl orange | Orange | Dark green | Green | No color change |
| 3 | Ethyl orange | Pink | Brown | Dark pink | Brown |
| 4 | Bromophenol blue | Yellow green | Dark green | No color change | No color change |
| 5 | Bromophenol blue + Methyl red | Brick red | No color change | Pink red | No color change |
| 6 | Bromocresol green | Orange | Orange green | No color change | No color change |

While certain representative embodiments and details have been shown for purposes of illustrating the invention, it will be apparent to those skilled in the art that various changes in the compositions and methods disclosed herein may be made without departing from the scope of the invention, which is defined in the appended claims.

What is claimed is:

1. A water-based chemical indicator ink for ethylene oxide sterilization processes containing:
   at least one pH indicator dye selected from the group consisting of Bromocresol green, Bromophenol blue, Methyl red, Ethyl orange, and combinations thereof; and
   a powdered and crystallized hexahydrate metal salt.

2. The water-based chemical indicator ink of claim 1 wherein said pH indicator dye undergoes an irreversible color change when exposed to ethylene oxide vapor in the presence of low-temperature steam.

3. The water-based chemical indicator ink of claim 2 wherein said low-temperature steam has a temperature of less then about 145° F.

4. The water-based chemical indicator ink of claim 1 wherein said pH indicator dye does not undergo a color change when exposed to formaldehyde gas, high-temperature steam, dry heat, or combinations thereof.

5. The water-based chemical indicator ink of claim 2 wherein said pH indicator dye undergoes a color change when exposed to formaldehyde gas, high-temperature steam, dry heat, or combinations thereof, that is different than is obtained when exposed to ethylene oxide vapor.

6. The water-based chemical indicator ink of claim 1 wherein said water-based chemical indicator ink is an aqueous ink solution.

7. The water-based chemical indicator ink of claim 6 wherein said aqueous ink solution comprises said pH indicator dye dissolved in water.

8. The water-based chemical indicator ink of claim 1 further containing an acidic compound, wherein said acidic compound retards a color change of said water-based chemical indicator ink.

9. The water-based chemical indicator ink of claim 8 wherein said acidic compound is citric acid.

10. The water-based chemical indicator ink of claim 1 further comprising a white pigment.

11. The water-based chemical indicator ink of claim 10 wherein said white pigment is titanium dioxide.

12. The water-based chemical indicator ink of claim 1 further containing a binder.

13. The water-based chemical indicator ink of claim 12 wherein said binder is a polymeric material.

14. The water-based chemical indicator ink of claim 13 wherein said polymeric material is selected from the group consisting of polyvinyl alcohol, methyl cellulose, and combinations thereof.

15. A water-based chemical indicator ink for ethylene oxide sterilization processes containing a combination pH indicator dye selected from the group consisting of Bromophenol blue and Ethyl orange, Bromophenol blue and Methyl red, Bromocresol green and Ethyl orange, Bromocresol green and Bromophenol blue, and Methyl red and Ethyl orange.

16. A water-based chemical indicator ink for ethylene oxide sterilization processes containing a combination pH indicator dye selected from the group consisting of Bromophenol blue and Ethyl orange, Bromophenol blue and Methyl red, Bromocresol green end Ethyl orange, Bromocresol green and Methyl red, Bromocresol green arid Bromophenol blue, and Methyl red and Ethyl orange, wherein said water-based chemical indicator ink is an aqueous ink solution.

17. A water-based chemical indicator ink for ethylene oxide sterilization processes containing:
   at least one pH indicator dye selected from the group consisting of Bromocresol green, Bromophenol blue, Methyl red, Ethyl orange, and combinations thereof; and
   at least one thickening agent selected from the group consisting of hydrous aluminum silicates, hydrous magnesium silicates, and combinations thereof.

18. A water-based chemical indicator ink for ethylene oxide sterilization processes containing:
   at least one pH indicator dye selected from the group consisting of Bromocresol green, Bromophenol blue, Methyl red, Ethyl orange, and combinations thereof; and
   a foam suppressor, wherein said foam suppressor is an aliphatic polyol blend.

* * * * *

UNITED STATES PATENT AND TRADEMARK OFFICE
CERTIFICATE OF CORRECTION

PATENT NO. : 6,800,124 B2
DATED : October 5, 2004
INVENTOR(S) : Puntambekar

Page 1 of 1

It is certified that error appears in the above-identified patent and that said Letters Patent is hereby corrected as shown below:

<u>Column 8,</u>
Line 43, "green end" should read -- green and --
Line 44, "green arid" should read -- green and --

Signed and Sealed this

Twenty-sixth Day of April, 2005

JON W. DUDAS
*Director of the United States Patent and Trademark Office*